United States Patent
Tagawa

(10) Patent No.: US 7,458,994 B2
(45) Date of Patent: Dec. 2, 2008

(54) HAIR DYE

(76) Inventor: Sadao Tagawa, 5-2603 Uedayama, Tenpaku-ku, Nagoya-si, Aichi-Ken (JP)

( * ) Notice: Subject to any disclaimer, the term of this patent is extended or adjusted under 35 U.S.C. 154(b) by 1 day.

(21) Appl. No.: 11/444,951

(22) Filed: Jun. 2, 2006

(65) Prior Publication Data

US 2007/0226918 A1    Oct. 4, 2007

(30) Foreign Application Priority Data

Jun. 2, 2005    (JP)    ............................... 2005-162931

(51) Int. Cl.
*A61Q 5/10*    (2006.01)
(52) U.S. Cl. ....................... 8/405; 8/406; 8/410; 8/428; 8/435; 8/604; 8/646
(58) Field of Classification Search ............ 8/405, 8/406, 410, 428, 435, 604, 646
See application file for complete search history.

(56) References Cited

U.S. PATENT DOCUMENTS 6,022,381 A * 2/2000 Dias et al. ...................... 8/406

OTHER PUBLICATIONS

English Abstract of the Japanese Patent No. JP 410265353A (1998).*
English Abstract of the Japanese Patent No. 408165227A (1996).*

* cited by examiner

*Primary Examiner*—Eisa B Elhilo
(74) *Attorney, Agent, or Firm*—DeLio & Peterson, LLC; Peter W. Peterson

(57) ABSTRACT

A composition and kit for hair dyeing comprising a first liquid containing an alkaline ingredient and an oxidation dye and a second liquid containing an oxidant wherein the improvement being the addition of a chlorophyll derivative, such as sodium iron chlorophyllin, into the first liquid.

12 Claims, No Drawings

HAIR DYE

FIELD OF THE INVENTION

The present invention relates to a hair dye composition that can effectively decrease any damage to the scalp and hair and effectively decrease the time period for the hair dyeing process.

BACKGROUND OF THE INVENTION

In general, the oxidizing hair dye is comprised of a first liquid, which contains the main ingredient of the dyestuff intermediate called the oxidation dye and the alkaline agent, such as ammonia, and is generally adjusted to the pH of 9-11, and a second liquid which generally contains 3-6% hydrogen peroxide and a small amount of stabilizer and is generally adjusted to the pH of 2-3. The first liquid and the second liquid are mixed just before dyeing the hair, and then the mixture is applied to the hair. The alkaline agent contained in the first liquid has the function to improve the penetration and absorption of the dye into the hair and to generate oxygen by decomposing the hydrogen peroxide in the second liquid. Moreover, the hydrogen peroxide in the second liquid has the function to decompose the melanin pigment in the hair with the oxygen generated by the reaction with the alkaline agent, and the function to allow oxidative polymerization of the dyestuff intermediate in the first liquid and form an insoluble colored pigment in the hair.

Consumers can now purchase hair dye kits from local market stores. The actual bleaching process, which involves bleaching melanin or color from the hair fiber, provides inconsistent results. This is true whether the whole head is being bleached or only highlighting select strands.

In a conventional oxidizing hair dye, it takes about 20 or 40 minutes until the insoluble pigment is formed by the oxidative polymerization of the dyestuff intermediate in the first liquid. Therefore a person is forced to remain still for a long time, and also there is the risk of suffering skin rash of the scalp or damaged hair because the scalp and the hair are exposed to the alkaline agent for a long time.

Accordingly, there is a need for a process and compositions that provide a person friendly, speedy system for bleaching the entire head of hair or highlighting select strands which provides custom colored highlights with salon quality results. This system should be able to provide consistent results in lightening and coloring virgin hair as well as hair that has already been oxidatively colored. The system can be used at home or in the salon.

In beauty salons, highlights are expensive and generally the entire process takes from one to three hours. Typically strands of hair selected for highlighting are arranged on many small pieces of metal foil which are positioned throughout the hair based upon the judgment of the beautician. The strands on the foil are painted with the highlighting or bleach for the appropriate period of time. The foils are then individually removed from the hair and the hair is rinsed well with water to remove all traces of the highlighting composition.

An object of the present invention is to provide a new hair dye which can decrease the damage to the scalp and the hair and effectively reduce the time period for the hair dye process.

Another object of the present invention is to provide a composition for hair dye that provides custom color such that the color is the one desired by the person and correlates to the color charts provided by the manufacturer.

It is another object of the present invention to provide a kit for hair dyeing that employs a novel composition that is contained in the oxidation dye composition component of the kit.

SUMMARY OF THE INVENTION

The invention is directed to a hair dye comprising a first liquid that contains an alkaline composition, an oxidation dye composition and a chlorophyll composition; and a second liquid comprising an oxidant composition.

Another embodiment of the invention is directed to a hair dye component for a hair dye kit in which the component comprising an alkaline composition, an oxidation dye composition and a chlorophyll composition.

Typically, hair dye kits include a plastic cap pierced with holes in a predetermined pattern. The consumer pulls the hair through the holes with a device that looks somewhat like a crochet hook. The select hairs are then treated with the highlighting composition for a period of time ranging from 30 to 60 minutes. The hair is rinsed with water and shampooed. In accordance with the present invention the time for dyeing can be effectively reduced to 10 minutes or less.

The chlorophyll composition could be a chlorophyll derivative in which the meaning should be one that has the chlorophyll frame and includes the chlorophyll extracted from a natural product, and the chlorophyll in which its central metal element is substituted. Preferably the chlorophyll derivative can be a metal salt formed by hydrolysis and more preferably would be sodium iron chlorophyllin.

The amount of the chlorophyll derivative added to the first liquid is preferably between about 0.007% and about 0.04% and more preferably between 0.01% and 0.02% of the total weight of the composition in the first liquid. The reason for this amount is that a sufficient coloring promotional effect is obtained, and that the undesirable side reaction, such as the formation of an insoluble polymer due to the reaction with the oxidizing dye during storage and the formation of the iron hydroxide due to the reaction with the alkaline ingredient, can be inhibited.

Moreover, it is desirable to mix an anti-inflammatory agent to the first liquid in order to prevent the inflammation, etc., of the scalp caused by the alkaline agent. An example of the anti-inflammatory agent is one that contains a plant extract as an active component such as one containing a comfrey extract, a linden extract, a peony extract and mixtures thereof.

Preferably, it is desirable to use an organic amine which has a weak alkalinity and low acridity.

According to this invention, the reaction between the oxidizing dye in the first liquid and the oxidant included in the second liquid is promoted and completed in a short time by adding the chlorophyll derivative to the first liquid, and the effect on the hair and the scalp can be reduced.

BEST MODE FOR CARRYING OUT THE INVENTION

Hereafter, the performing mode of this invention is explained in detail. This invention is characterized by a hair dye comprised of the first liquid, which contains the alkaline agent and the oxidizing dye, and the second liquid, which contains the oxidant, wherein the improvement involves the first liquid containing a chlorophyll derivative.

In this invention, sodium iron chlorophyllin is preferably used as the chlorophyll derivative. It is desirable that the amount of sodium iron chlorophyllin mixed in the first liquid is preferably between 0.01% and 0.02% of the total weight of the first liquid. Within this preferred range, a sufficient coloring promotion effect can be demonstrated, and the undesirable side reaction, such as the formation of an insoluble polymer due to the reaction with the oxidizing dye in the first liquid during storage and the formation of the iron hydroxide due to the reaction with the alkaline agent, can be inhibited.

Preferably, the alkaline agent is an alkalescent organic amine although there is no restriction if it is the one usually used for the hair dye as the alkaline agent because when sodium iron chlorophyllin is used as the chlorophyll derivative and a strong alkaline agent is used, in particular, when the amount of sodium iron chlorophyllin is high, the coloring might be obstructed due to the formation of iron hydroxide by the reaction of the included iron with the alkaline agent. Moreover, the effect on the hair and the scalp can be reduced due to its low stimulant action. For instance, mono-ethanoilamine, diethanolamine, triethanolamine, etc., are enumerated as organic amines.

As the oxidizing dye, the combination of the coupling agent and the dyestuff intermediate, which is usually used for the hair dye, can be used. As for the dyestuff medium, p-phenyl diamine, toluenediamine, p-aminophenol, etc., can be used. Moreover, as for the coupling agent, m-phenylene diamine, m-aminophenol, resorcin, diaminopyridine, naphthol, amino cresol, etc., can be used.

As for the oxidant, a hydrogen peroxide can be preferably used for the hair dye. The content of the hydrogen peroxide is preferably to be between 3% and 6% of the total weight of the second liquid.

It is desirable to add an anti-inflammatory agent in order to prevent inflammation of the scalp caused by the alkaline agent in the first liquid. As for the anti-inflammatory agent, the one which contains the plant extract as the active constituent can be used, for instance, "PHYTOBLEND (registered trademark) TIPS" manufactured by Ichimaru Pharcos Co., Ltd., can be used as the preferable example. This anti-inflammatory agent, which contains the "comfrey extract" (No. 520476), the "linden extract" (No. 520550) and the "peony extract" (No. 523205) as the active components, are all listed in the nonstandard cosmetics raw material ingredient specifications.

As for the solvent of the first and second liquids, in particular, there is no restriction if it is the one currently used for the hair dye, for example, purified water can be used.

Besides the above-described components, the first or the second liquid can contain a cream base agent, a surface active agent, an emulsifying agent, a perfume, preservative, a pH adjusting agent, associative thickeners, and mixtures thereof In the subject invention, it is preferable to adjust the pH of the mixture of the first liquid and the second liquid to be effectively neutral-alkalescence in the range of 6.0-8.6. As a result, the effect on the hair and the scalp can be reduced. Specifically, when the first liquid and the second liquid are mixed in the ratio of 1:1, such a condition can be achieved by making the pH of the first liquid alkaline at about 8.6 using the alkalescent organic amine as the alkaline agent, and making the pH of the second liquid 2.0-4.0 using the pH adjuster.

EXAMPLE 1

1. Preparation of the Hair Dye
(1) Blending of the First Liquid

The following components were dissolved in purified water to make 100 weight parts, and this solution was defined as the first liquid: 1.2 weight parts of p-phenylene diamine as the dyestuff intermediate, 0.3 weight parts of m-phenylene diamine and 0.1 weight parts of 2,6-diaminopyridine as the coupling agents, 0.01 weight parts of sodium iron chlorophyllin as the chlorophyll derivative, 0.1 weight parts "PHYTOBLEND (registered trademark) TIPS" (manufactured by Ichimaru Pharcos Co., Ltd.) As the anti-inflammatory agent, 5.0 weight parts of stearyl alcohol, 1.0 weight parts of cetyl alcohol, 2.0 weight parts of myristic acid isopropyl as the cream base agents, 1.5 weight parts of polyoxyethylene cetyl ether, 3.0 weight parts of stearyl trimethylammonium chloride as the emulsifying agent, 0.3 weight parts of monoethanolamine as the alkaline agent and 0.2 weight parts of perfume.

(2) Blending of the Second Liquid

Six weight parts of hydrogen peroxide as the oxidant, and a small amount of phenacetin as the stabilizer were mixed with purified water. The pH of this solution was adjusted to 3.0 using phosphoric acid and disodium dihydrogen pyrophosphate, and the entire volume was made to 100 weight parts.

(3) Blending of Hair Dye

The first and the second liquids were mixed in the ration 1:1 just before use, which created the hair dye. The pH of the hair dye was 7.6.

(4) Dyeing Test

About a 2 g of a packet of yak's white fur was coated with the hair dye prepared as above, and then it was left to stand. The time dependency of its color tone was then observed.

(5) Hair Coloring Test

Twenty adults having their hair streaked with gray were chosen as the subjects, and the hair of the subjects were dyed using the hair dye prepared as above. The treatment time and the color tone, texture and gloss of the hair after the hair dyeing were evaluated.

EXAMPLE 2

For the preparation of the first liquid, 1.1 weight parts of p-phenylene diamine and 0.4 weight parts of p-aminophenol as the dyestuff medium, and 0.2 weight parts of m-aminophenol and 0.3 weight parts of resorcin as the coupling agents were used. The hair dye was prepared under the same conditions as for example 1 except for the above described conditions, and the dyeing test was done.

EXAMPLE 3

For the preparation of the first liquid, 1.1 weight parts of p-phenylene diamine and 0.4 weight parts of p-aminophenol as the dyestuff medium, and 0.2 weight parts of m-aminophenol and 0.3 weight parts of resorcin as the coupling agents, and 1.5 weight parts of monoethanolamine as the alkaline agent were used. The hair dye was prepared under the same conditions as for example 1 except for the above described conditions, and the dyeing test was done.

EXAMPLE 4

For the preparation of the first liquid, 0.5 weight parts of p-phenylene diamine and 0.2 weight parts of p-aminophenol as the dyestuff medium, 0.2 weight parts of m-aminophenol and 0.4 weight parts of resorcin and 0-25 weight parts of o-aminophenol as the coupling agents, and 1.5 weight parts of monoethanolamine as the alkaline agent were used. The hair dye was prepared under the same conditions as for example 1 except for the above described conditions, and the dyeing test was done.

COMPARATIVE EXAMPLE

A commercially available home use hair dye was used and the dyeing test was done under the same conditions as for example 1.

TEST RESULTS

The blending ratio of each component in the first liquid and the second liquid is indicated in Table 1. The results of the dyeing test and the pH of the hair dye are shown in Table 2. The results of the hair dyeing test are shown in Table 3. In Table 3, the results of the evaluation of the texture and the gloss are expressed by the symbols Δ and ○. The ones equivalent to the comparison example were noted by the Δ symbol, and the more excellent one compared to the comparison example was noted by the ○ symbol.

TABLE 2

|  | pH | Color development time (minute) | Color tone |
|---|---|---|---|
| Example 1 | 7.6 | 5 | Blue black |
| Example 2 | 7.6 | 8 | Burnt umber |
| Example 3 | 7.5 | 8 | Fuscous |
| Example 4 | 7.8 | 5 | Reddish brown |
| Comparison example | 9.8 | 30 | Burnt umber |

TABLE 1

|  |  | Example 1 | Example 2 | Example 3 | Example 4 |
|---|---|---|---|---|---|
| The first liquid | [Dyestuff intermediate] | | | | |
| | p-phenylene diamine | 1.2 | 1.1 | 1.1 | 0.5 |
| | p-aminophenol | | 0.4 | 0.4 | 0.2 |
| | [Coupling agent] | | | | |
| | m-phenylene diamine | 0.3 | | | |
| | m-aminophenol | | 0.2 | 0.2 | 0.2 |
| | Resorcin | | 0.3 | 0.3 | 0.4 |
| | 2,6-diaminopyridine | 0.1 | | | |
| | o-aminophenol | | | | 0.25 |
| | [Chlorophyll, derivative] | | | | |
| | Sodium iron chlorophyllin | 0.01 | 0.01 | 0.01 | 0.01 |
| | [Antiinflammatory agent] | | | | |
| | PHYTOBLEND TIPS | 0.1 | 0.1 | 0.1 | 0.1 |
| | [Cream base agent] | | | | |
| | Stearyl alcohol | 5.0 | 5.0 | 5.0 | 5.0 |
| | Cetyl alcohol | 1.0 | 1.0 | 1.0 | 1.0 |
| | Myristic acid isopropyl | 2.0 | 2.0 | 2.0 | 2.0 |
| | [Emulsifying agent] | | | | |
| | Polyoxyethylene cetyl ether | 1.5 | 1.5 | 1.5 | 1.5 |
| | Stearyl trimethylammonium chloride | 3.0 | 3.0 | 3.0 | 3.0 |
| | [Alkaline agent] | | | | |
| | Mono ethanolamine | 0.3 | 0.3 | 1.5 | 1.5 |
| | Perfumes | 0.2 | 0.2 | 0.2 | 0.2 |
| | Purified water | Appropriate quantity | | | |
| | Total | 100.0 | 100.0 | 100.0 | 100.0 |
| The second liquid | [Oxidant] | | | | |
| | Hydrogen peroxide | 6.0 | 6.0 | 6.0 | 6.0 |
| | [Stabilizer] | | | | |
| | Phenacetin | A small amount | | | |
| | [pH adjuster] | | | | |
| | Phosphoric acid | Until making the pH to 3.0 | | | |
| | Disodium dihydrogen pyrophosphate | | | | |
| | Purified water | Appropriate quantity | | | |
| | Total | 100.0 | 100.0 | 100.0 | 100.0 |

TABLE 3

| | Color development time (minute) | Color tone | Texture | Gloss |
|---|---|---|---|---|
| Example 1 | 5 | Even blue black | ○ | ○ |
| Example 2 | 8 | Even burnt umber | ○ | Δ |
| Example 3 | 8 | Even fuscous | ○ | ○ |
| Example 4 | 5 | Even reddish brown | ○ | Δ |
| Comparison example | 30 | Even burnt umber | — | — |

Table 2 and Table 3 show that the pH of the hair dye for examples 1 through 4 were adjusted to almost neutral of 7.5 to 7.8. Moreover, the color development time has been significantly shortened to 5-8 minutes compared to 30 minutes for the comparison hair dye. Furthermore, the results in which there was no irregular coloring and that the texture and the gloss was equivalent or superior to the conventional one was obtained.

Based on the above described results, it has been determined that these invented hair dyes are capable to significantly decrease the damage to the user's hair and scalp and to the hand of its applier, and that the quality of the dyeing is equivalent or superior, to the conventional one.

With the foregoing description of the invention, those skilled in the art will appreciate that modifications may be made to the invention without departing from the spirit thereof. Therefore, it is not intended that the scope of the invention be limited to the specific embodiments illustrated and described.

The invention claimed is:

1. A hair dye comprising a first liquid that contains an alkaline composition, an oxidation dye composition and a sodium iron chlorophyllin composition; and a second liquid comprising an oxidant composition.

2. The hair dye of claim 1 wherein a mixture comprising comfrey extract, linden extract and peony extract is also added to the first liquid as an anti-inflammatory composition.

3. The hair dye of claim 1 wherein the alkaline composition is an organic amine.

4. A hair dye comprising a first liquid that contains an alkaline composition, an oxidation dye composition and a sodium iron chlorophyllin composition between about 0.01% and about 0.02% of the total weight of the compositions in the first liquid; and a second liquid comprising an oxidant composition.

5. The hair dye of claim 4 wherein a mixture comprising comfrey extract, linden extract and peony extract is also added to the first liquid as an anti-inflammatory composition.

6. The hair dye of claim 4 wherein the alkaline composition is an organic amine.

7. A hair dye component for a hair dye kit, the component comprising an alkaline composition, an oxidation dye composition and a sodium iron chlorophyllin composition.

8. The hair dye component of claim 7 wherein a mixture comprising comfrey extract, linden extract and peony extract is also added to the first liquid as an anti-inflammatory composition.

9. The hair dye component of claim 7 wherein the alkaline composition is an organic amine.

10. A hair dye component for a hair dye kit, the component comprising an alkaline composition, an oxidation dye composition and a sodium iron chlorophyllin composition between about 0.01% and about 0.02% of the total weight of the compositions.

11. The hair dye component of claim 10 wherein a mixture comprising comfrey extract, linden extract and peony extract is also added to the first liquid as an anti-inflammatory composition.

12. The hair dye component of claim 10 wherein the alkaline composition is an organic amine.

* * * * *